United States Patent
Katz et al.

(10) Patent No.: US 6,809,115 B2
(45) Date of Patent: Oct. 26, 2004

(54) METHODS AND COMPOSITIONS FOR THE TREATMENT OF DIABETES, THE REDUCTION OF BODY FAT, IMPROVEMENT OF INSULIN SENSITIVITY, REDUCTION OF HYPERGLYCEMIA, AND REDUCTION OF HYPERCHOLESTEROLEMIA WITH CHROMIUM COMPLEXES, CONJUGATED FATTY ACIDS, AND/OR CONJUGATED FATTY ALCOHOLS

(75) Inventors: David P. Katz, Dobbs Ferry, NY (US); James R. Komorowski, Trumbull, CT (US); Danielle Greenberg, Waccabuc, NY (US)

(73) Assignee: Nutrition 21, Inc., Purchase, NY (US)

( * ) Notice: Subject to any disclaimer, the term of this patent is extended or adjusted under 35 U.S.C. 154(b) by 0 days.

(21) Appl. No.: 09/957,876

(22) Filed: Sep. 20, 2001

(65) Prior Publication Data

US 2002/0081315 A1 Jun. 27, 2002

Related U.S. Application Data

(60) Provisional application No. 60/234,474, filed on Sep. 21, 2000, and provisional application No. 60/296,688, filed on Jun. 6, 2001.

(51) Int. Cl.[7] .......................... A61K 31/20; A61K 31/28

(52) U.S. Cl. .......................... 514/505; 514/492; 514/558

(58) Field of Search ................................ 514/505, 492, 514/558, 951, 188; 424/451, 725, 489, 514, 951

(56) References Cited

U.S. PATENT DOCUMENTS

| | | |
|---|---|---|
| 3,899,476 A | 8/1975 | Ward |
| 3,923,768 A | 12/1975 | Powers et al. |
| 4,056,637 A | 11/1977 | Hagiwara et al. |
| 4,393,043 A | 7/1983 | Koulbanis et al. |

(List continued on next page.)

FOREIGN PATENT DOCUMENTS

| | | |
|---|---|---|
| EP | 0 839 897 | 5/1998 |
| WO | WO 96/23811 | 8/1996 |
| WO | WO 96/35421 | 11/1996 |
| WO | WO 97/46118 | 12/1997 |
| WO | WO 97/46230 | 12/1997 |
| WO | WO 98/24422 | 6/1998 |

(List continued on next page.)

OTHER PUBLICATIONS

Product Alert: Natrol Supplement –CLA–1000; CLA–750 Manufacturer: Natrol, Inc.; Jun. 1997, One page full text.*
Courtesy copy of International Search Report in 2 pages, dated Nov. 25, 2002.
Absher, et al. (1999) The retardation of vasculopathy induced by attenuation of insulin resistance in the corpulent JCR:LA–cp rate is reflected by decreased vascular smooth muscle cell proliferation in vivo. Atherosclerosis. Abstract in 2 pages.

(List continued on next page.)

Primary Examiner—Patricia Leith
(74) Attorney, Agent, or Firm—Knobbe Martens Olson & Bear LLP (57) ABSTRACT

A composition for treating insulin-dependent diabetes, reducing body fat, improving insulin sensitivity, reducing hyperglycemia, and reducing hypercholesterolemia with at least one chromium complex and a conjugated fatty acid or conjugated fatty alcohol is disclosed. A method of treating a subject suffering from insulin-dependent diabetes by administering a composition that includes at least one chromium complex and a conjugated fatty acid or conjugated fatty alcohol is similarly provided. The administration of a composition containing an effective dose of at least one chromium complex and a conjugated fatty acid or conjugated fatty alcohol for the treatment of obesity is likewise provided.

13 Claims, 3 Drawing Sheets

The Effect of CP + CLA on Glucose Uptake in Human Skeletal Muscle Culture

U.S. PATENT DOCUMENTS

| | | | |
|---|---|---|---|
| 4,407,821 A | 10/1983 | Mendy | |
| 4,871,768 A | 10/1989 | Bistrian et al. | |
| 4,954,492 A | 9/1990 | Jensen | |
| 5,017,614 A | 5/1991 | Pariza et al. | |
| 5,053,534 A | 10/1991 | Cosgrove | |
| 5,070,104 A | 12/1991 | Pariza et al. | |
| 5,087,623 A | 2/1992 | Boynton et al. | |
| 5,087,624 A | 2/1992 | Boynton et al. | |
| RE33,988 E | 7/1992 | Evans | |
| 5,175,156 A | 12/1992 | Boynton et al. | |
| 5,194,615 A | 3/1993 | Jensen | |
| 5,194,640 A | 3/1993 | Cosgrove et al. | |
| 5,208,356 A | 5/1993 | Pariza et al. | |
| 5,428,072 A | 6/1995 | Cook et al. | |
| 5,430,066 A | 7/1995 | Cook et al. | |
| 5,543,405 A | 8/1996 | Keown et al. | |
| 5,554,646 A | 9/1996 | Cook et al. | |
| 5,760,082 A | 6/1998 | Cook et al. | |
| 5,770,247 A | 6/1998 | Satter et al. | |
| 5,789,401 A | 8/1998 | McCarty | |
| 5,804,210 A | 9/1998 | Cook et al. | |
| 5,814,663 A | 9/1998 | Cook et al. | |
| 5,837,733 A | 11/1998 | Pariza et al. | |
| 5,851,572 A | 12/1998 | Cook et al. | |
| 5,855,917 A | 1/1999 | Cook et al. | |
| 5,855,949 A | 1/1999 | McLean | |
| 5,856,149 A | 1/1999 | Pariza et al. | |
| 5,892,074 A | 4/1999 | Seidel | |
| 5,986,116 A | 11/1999 | Iwata et al. | |
| 6,015,833 A | 1/2000 | Saebo | |
| 6,019,874 A | 2/2000 | Berg et al. | |
| 6,020,377 A | 2/2000 | O'Quinn et al. | |
| 6,020,378 A | 2/2000 | Cook et al. | |
| 6,034,132 A | 3/2000 | Remmereit | |
| 6,042,869 A | 3/2000 | Remmereit | |
| 6,060,087 A | 5/2000 | Cook et al. | |
| 6,060,514 A | 5/2000 | Jerome et al. | |
| 6,077,525 A | 6/2000 | Vanderhoek | |
| 6,093,711 A * | 7/2000 | De la Harpe et al. | 514/188 |
| 6,153,774 A | 11/2000 | Seidel | |
| 6,159,525 A | 12/2000 | Lievense et al. | |
| 6,177,580 B1 | 1/2001 | Timmermann et al. | |
| 6,184,009 B1 | 2/2001 | Cain et al. | |
| 6,203,843 B1 | 3/2001 | Remmereit | |
| 6,214,372 B1 | 4/2001 | Jerome et al. | |
| 6,225,486 B1 | 5/2001 | Saebo et al. | |
| 6,242,621 B1 | 6/2001 | Jerome et al. | |
| 6,333,353 B2 | 12/2001 | Saebo et al. | |
| 6,413,545 B1 * | 7/2002 | Alvair et al. | 424/451 |

FOREIGN PATENT DOCUMENTS

| | | |
|---|---|---|
| WO | WO 98/33494 | 8/1998 |
| WO | WO 98/37873 | 9/1998 |
| WO | WO 98/48641 | 11/1998 |
| WO | WO 99/52382 | 10/1999 |
| WO | WO 99/56558 | 11/1999 |
| WO | WO 00/12080 | 3/2000 |
| WO | WO 00/35300 | 6/2000 |
| WO | WO 00/57720 | 10/2000 |
| WO | WO 02/09691 | 2/2002 |
| WO | WO 02/09692 | 2/2002 |
| WO | WO 02/09693 | 2/2002 |
| WO | WO 02/09725 | 2/2002 |

OTHER PUBLICATIONS

Azain, et al. (2000) Dietary conjugated linoleic acid reduces rat adipose tissue cell size rahter than cell number. J Nutri. 130:1548–1554.

Atkinson, R.L. (2000) Clinical implications for CLA in the treatment of obesity. Communication in 1 page.

Aydin, et al. (1998) Role of dietary oils in prevention of CLA–induced chick embryonic mortality and egg properties. Annual Report, Food Research Institute. 52–56.

Badinga, et al. (2001) Performance and lipid deposition in broilers fed conjugated linoleic acid, J. Anim. Sci. vol. 79, Suppl. 1, Abstract, page 194.

Bauman, et al. (2001) Conjugated linoleic acid (CLA) and lipid metabolism in lactating cows. J. Anim. Sci. vol. 79, Suppl. 1, Abstract p. 193.

Baumgard, et al. (2000) Identification of the conjugated linoelic acid isomers that inhibits mild fat synthesis. Am. J. Physiol. Regulatory Integrative Comp. Physiol. 278:R179–R184.

Baumgard, et al. (2001) Milk fat synthesis in dairy cows is progressively reduced by increasing amounts of trans–10, cis–12 conjugated linoleic acid (CLA). J. Anim. Sci . vol. 79, Suppl. 1, Abstract, p. 193.

Belury, M.A. (1995) Conjugated dienoic linoleate: A polyunsaturated fatty acid with unique chemoprotective properties. Nutrition Reviews. 53:(4)83–89.

Belury, M.A. (1997) Conjugated linoleic acid modulates hepatic lipid composition in mice. Lipids. Abstract in 2 pages.

Belury, M.A. (2000) Role of conjungated linoleic acid (CLA) in the management of type 2 diabetes: evidence from Zuker diabetic (FA/FA) rats and human subjects. American Chemical Society, vol. 220, abstract No. 26 in 1 page.

Blankson, et al. (2000) conjugated linoleic acid reduces body fat mass in overweight and obese humans. J Nutr. 130:2943–2948.

Bonilla, et al. (2001) Effect of a pharmaceological activation of PPAR on the expresion of RAR and TR in rat liver. J Physiol Biochem. Abstract in 2 pages.

Bontempo, et al. (2001) Dietary conjugated linoleic acid (CLA) influence the immune response in weanling piglets. J. Anim. Sci. vol. 79 Suppl. Abstract, p. 194.

Brodie et al. (1999) Conjugated lineoleic acid inhibits differentiation of pre–and post–confluent 3T3–L1 preadipocytes but inhibits cell proliferation only in preconfluent cells. J. Nutr. 129:602–605.

Chinetti, et al. (2001) Preoxisome proliferator–activated receptors (PPARs): nuclear receptors with functions in the vascular wall. Z. Kardiol 90:Suppl. 3, III/125–III/132.

Choi, et al. (2000) Effects of CLA on Adipocytes. 2000 Annual report. Food Research Institute 53–54.

Cook, M. (2001) Conjugated linoleic acid (CLA) in growth and development: Mechanisms involving immunity and porstanoids. J. Anim. Sci. vol. 79, Suppl. 1. Abstract, p. 194.

Corino, et al. (2001) Dietary conjugated lineolic acid (CLA) influence the lipogenic enzyme activities in adipose tissue and liver of rattit J. Anim. Sci. vol. 79, Suppl. 1. Abstract, p. 194.

DeLany et al., (1999) Conjugated linoleic acid rapidly reduces body fat content in mice without affecting energy intake. Am J Physiol. Abstract in 1 page.

Dhiman, et al., (1999) Conjugated linoleic acid content of milk from cows fed different diets. J Dairy Sci. Abstract in 1 page.

Dhiman, et al., (2000) Enhancing the CLA content of cow's milk. Food Research Institute. Pg. 56.

Dimitriadis, et al. (1996) Lipoprotein composition in NIDDM:effects of dietary oleic acid on the composition, oxidisability and function of low and high density lipproteins. Diabetologia. PMID: 8781762, UI: 96375451.

Ferreira, et al. (1997) Effects of conjugated linoleci acid (CLA) supplementation during resistance training on body composition and strength. Abstract from 1997 NSCA Conference, p. 280.

Haycock, B. (2001) Howz it work?: CLA http://musclemonthly.com/articles/010401-1-haycock-howz-it-work.htm in seven pages.

Houseknecht, et al. (1998) Dietary conjugated linoleic acid normalizes impaired glucose tolerance in the Zucker diabetic fatty fa/fa rat. Biochem. Biophys. Res Commun. Abstract in 1 page.

Houseknecht, K.L. (1998) Compound in meat prevents diabetes. Purdue University News Journal article in 4 pages.

King, I. B. (1996) Lipids in foods: chemistry and nomenclature. Handbook of Lipids in Human Nutrition. 3–11.

Lee, et al. (1994) Conjugated linoleic acid and atherosclerosis in rabbits. Atherosclerosis, Abstract 1 page.

Liu, et al., (1997) Conjugated linoleic acid moduluation of phorbol ester-induced events in murine keratinocytes. Lipids. Abstract 1 page.

Lowery, et al. (2000) 1038 Conjugated linoleic acid enhnaces muscle size and strength gains in novice bodybuilders. Medicine and Science in Sports and Exercise, Abstract, p. S182.

Mathe, D. (1995) Dyslipidemia and diabetes: animal models, Diabete, Metab. Abstract 1 page.

Mersmann, et al. (2001) Mechanisms for conjugated linoleic acid-mediated reduction in fat deposition. J. Anim. Sci. vol. 79, Suppl. 1. Abstract, pp. 193–194.

Moya-Camarena, et al. (1999) Species differences in the metabolism and regulation of gene expression by conjugated linoleic acid. Nutrition Reviews. 57(11):336–340.

Moya-Camarena, et al. (1999) Conjugated linoleic acid is a potent naturally occurring ligand and activator of PPARα, Journal of Lipid Research, 40:1426–1433.

Nicolosi, et al. (1997) Dietary conjugated linoleic acid reduces plasma lipoproteins and early aortic atherosclerosis in hypercholesterolemic hamsters. Arter. 22(5):266–277.

Ostrowska, et al. (1999) Dietary conjugated linoleic acids increase lean tissue and dcecrease fat deposition in growing pigs. J Nutr. Abstract in 1 page.

Pariza, et al. (2000) Mechanisms of action of conjugated linoleic acid: evident and speculation. Proc Soc Exp Biol Med. Abstract in 1 page.

Pariza, et al. (1999) Conjugated linoleic acid and the control of cancer and obesity. Toxicol Sci. Abstract in 1 page.

Park, et al. (1999) Comparison of methylation procedures for conjugated linoleic acid (CLA). 1999 Annual Report, Food Research Institute, pp. 48–56.

Park, et al. (1999) Evidence that the trans-10,cis-12 isomer of conjugated linoleic acid includes body composition changes in mice. Lipids. Abstract in 1 page.

Park, et al. (1997) Effect of conjugated linoleic acid on body composition in mice. Lipids. 32:853–856.

Risérus, et al. (2001) Conjugated linoleic acid (CLA) reduced abdominal adipose tissue in obese middle-aged men with signes of the metabolic syndrome: a randomised controlled trial. International Journal of Obestiy. 25:1129–1135.

Rudel, L. L. (1999) Invited commentary atherosclerosis and conjugated linoleic acid. British Journal of Nutrition. 81:177–179.

Russell, et al. (1999) Glucose tolerance and insulin resistance in the JCR:LA-corpulent rat: effect of miglitol (Bay m1099). Metabolism. Abstract in 1 page.

Ryder, et al. (2001) Isomer-specific antidiabetic properties of conjugated linoleic acid. Diabetes. 50:1149–1157.

Sakono, et al. (1999) Dietary conjugated linoleic acid reciprocally modifies ketogenesis and lipid secretion by the rat liver. Lipids. Abstract in 1 page.

Schrezante et al. ((2000) Milk and Diabetes. Journal of the American College of Nutrition. 19(2):176S–190S.

Sebedio, et al. (1997) Metabolites of conjugated isomers of linoleic acid (CLA) in the rat. Biochim Biophys Acta. PMID: 9084496, UI:97238160 Abstract in 1 page.

Sippel, et al. (2001) The use of rumen-protected conjugated linoleic acid to reduce milk fat percentage in lactating dairy cattle. J. Anim. Sci. vol. 79, Suppl. 1, Abstract, p. 193.

Skinner, R. (1999) Medium-chain triglycerides and conjugated linoleic acid. Scan's Pulse. pp. 10–11.

Slim, et al. (1996) Susceptibility to hepatic oxidative stress in rabbits fed different animal and plant fats. J Am Coll Nutr. PMID: 8935445; UI 97089537 Abstract in 1 page.

Stangl, G. I. (2000) Conjugated linoleic acids exhibit a strong fat-to-lean partitioning effect, reduce serum VLDL lipids and redistribute tissue lipids in food-restricted rats. J. Nutri. 130:1140–1146.

Steinhart, C. (1996) Beef Facts: Conjugated linoleic acid and dietary beef—an update. National Cattlemen's Beef Assocation. Series No. FS/N 016, pp. 1–6.

Vanden Hauvel, et al. (2000) Evidence for a $PPAR_\gamma$-dependent mechanism of action for conjugated linolecia cid (CLA) in several cell types. American Chemical Society. vol. 220, Abstract #25.

West, et al. (1998) Effects of conjugated linoleic acid on body fat and energy metabolism in the mouse. Am J Physiool. PMID: 9727617, UI: 98394600 Abstract in 1 page.

Yamasaki, et al. (1999) Dietary Effect of conjugated linoleic acid on lipid levels in white adipose tissue of Sprague-Dawley rats. Biosci Biotechnol Biochem. Abstract 1 page.

Yuraweca, et al. (1999) Variations in isomer distribution in commercially available conjugated linoleci acid. Fett/Lipid. 101:277–282.

CLA building muscle and energy. LE magazine Apr. 1999. Various Abstract in 8 pages.

Anderson (1986) Chromium metabolism and its role in disease processes in man. Clinical Physiology and Biochemistry, Abstract in 1 page.

Bauer et al. (1998) Coated pharmaceutical dosage forms: Fundamentals, manufacturing techniques, biopharmaceutical aspects, test methods and raw materials. CRC Press, Washington, D.C. 81–85.

Boyle, Jr. et al. (1977) Chromium depletion in the pathogenesis of diabetes and antheroschlerosis. 1977) Southern Medical Journal, 70(12):1449–1453.

Carstensen, J.T. (1993) Pharmaceutical principles of solid dosage forms. Technomic Publishing Co., Inc., Lancaster, PA 228–230.

Cefalu et al. (1999) Effect of chromium picolinate on insulin sensitivity in vivo. J Trace Elem Exp Med. 12:71–83.

Kaats et al. (1998) A randomized, double–masked, placebo–controlled study of the effects of chromium picolinate supplmentation on body composition: a replication and extension of a previous study. Current Therapeutic Research. 59(6):379–388.

Kamath et al. (1997) Absorption retention and urinary excretion of chromium–51 in rats pretreated with indomethacin and dosed with dimethylprostaglandin $E_2$, misoprostol or prostacyclin[1,2,3]. J Nutr. 127:478–482.

Singh et al. (1986) Pharmacology of an extract of salai guggal ex–*Boswellia serrata,* a new non–steroid anti–inflammatory agent. Agents and Actions. 18:407–412.

Recommended Daily Allowances, Ninth Edition, 1980. National Academy of Sciences. Washington, D.C.

* cited by examiner

Figure 1: The Effect of Conjugated Linoleic Acid (CLA) on Glucose Uptake in Human Skeletal Muscle Culture Figure 2: The Effect of CP + CLA on Glucose Uptake in Human Skeletal Muscle Culture Figure 3: The Effect of CP + CLA on Glucose Uptake in Human Skeletal Muscle Culture
(Percent Increase Over Baseline)

METHODS AND COMPOSITIONS FOR THE TREATMENT OF DIABETES, THE REDUCTION OF BODY FAT, IMPROVEMENT OF INSULIN SENSITIVITY, REDUCTION OF HYPERGLYCEMIA, AND REDUCTION OF HYPERCHOLESTEROLEMIA WITH CHROMIUM COMPLEXES, CONJUGATED FATTY ACIDS, AND/OR CONJUGATED FATTY ALCOHOLS

This application claims priority to provisional application filed Sep. 21, 2000 having application No. 60/234,474, and provisional application filed Jun. 6, 2001 having application No. 60/296,688.

BACKGROUND OF THE INVENTION

1. Field of the Invention

The disclosed invention related to compositions and methods for the treatment of type 1 diabetes, reduction of body fat, improvement of insulin sensitivity, reduction of hyperglycemia, and reduction of hypercholesterolemia. Specifically, compositions comprising chromium complexes in combination with conjugated compounds such as isomers of conjugated fatty acids or conjugated fatty alcohols.

2. Description of the Related Art

Insulin-Dependent Diabetes

Diabetes is a chronic metabolic disorder which afflicts 16 million people in the United States, over one and one half million of whom have its most severe form, childhood diabetes (also called juvenile, type 1 or insulin-dependent diabetes). Insulin-dependent diabetes appears suddenly, most often in children and young adults, and progresses rapidly. In this form, the pancreas ceases to manufacture insulin, a hormone necessary to convert the food we eat into energy for the body. In the United States, diabetes is the fourth leading cause of death, killing more than 162,000 people each year. Notably, the mortality rate of patients with insulin-dependent diabetes increases dramatically after 15 years of disease duration. In addition, virtually every major organ system in the body is damaged by diabetes. Complications can include blindness, kidney failure, heart disease, stroke, amputation of extremities, loss of nerve sensation, early loss of teeth, high-risk pregnancies and babies born with birth defects.

Insulin resistance is characterized by reductions of glucose uptake in skeletal muscle. Currently, insulin injection is the only treatment method available for the over 1.5 million type 1 diabetics and becomes the eventual course of treatment for many of the more than 16 million type 2 diabetics in the United States. Nutritional therapies that positively impact glucose uptake in the face of insulin insufficiency would have a major impact on the long term treatment costs associated with diabetic care.

Obesity

More than half of U.S. adults are overweight and nearly one-quarter of the U.S. adults are considered to be obese. The increasing prevalence of overweight and obesity is a major public health concern, since obesity is associated with several chronic diseases. For example, overweight and obesity are known risk factors for diabetes, heart disease, stroke, hypertension, gallbladder disease, osteoarthritis, sleep apnea, and some forms of cancer such as uterine, breast, colorectal, kidney, and gallbladder. Furthermore, obesity is associated with high cholesterol, complications of pregnancy, menstrual irregularities, hirsutism, and increased surgical risk.

Drugs currently approved by the FDA for the treatment of obesity produce weight losses of about 10% of initial body weight at one year when used singly. Combination therapy with phentermine and fenfluramine produced weight losses of about 15% of initial body weight at one year. Phenylpropanolamine (PPA) is an over-the-counter drug that has not been tested for long term use and is recommended for use for only about 12 weeks. With the exception of PPA, all of these drugs require a physician's prescription and are generally quite expensive. Side effects occur with all these drugs. For example, the administration of fenfluramine and phentermine for the treatment of obesity resulted in cardiac valve damage in some patients and ultimately led to the withdrawal of fenfluramine from the market. Two of the newest drugs for the treatment of obesity have side effects that limit their use. Sibutramine increases blood pressure in a subset of patients, and orlistat may have unpleasant gastrointestinal side effects.

The Role of Chromium Complexes in the Treatment of Insulin-Dependent Maladies

Chromium picolinate is reported to produce modest weight loss and changes in body composition (Kaats, 1998, Cefalu, 1999). Chromium is a nutritionally essential trace element. The essentiality of chromium in the diet was established in 1959 by Schwartz, as cited in *Present Knowledge in Nutrition*, page 571, fifth edition (1984, the Nutrition Foundation, Washington, D.C.). Chromium depletion is characterized by the disturbance of glucose, lipid and protein metabolism and by a shortened lifespan. Chromium is essential for optimal insulin activity in all known insulin-dependent systems (Boyle et alN., *Southern Med. J.* 70:1449–1453, 1977). Insufficient dietary chromium has been linked to both maturity-onset diabetes and to cardiovascular disease.

The principal energy sources for the body are glucose and fatty acids. Chromium depletion results in biologically ineffective insulin and compromised glucose metabolism. Under these conditions, the body must rely primarily on lipid metabolism to meet its energy requirements, resulting in the production of excessive amounts of acetyl-CoA and ketone bodies. Some of the documented acetyl-CoA is diverted to increased cholesterol biosynthesis, resulting in hypercholesterolemia. Diabetes mellitus is characterized in large part by glycosuria, hypercholesterolemia, and often ketoacidosis. The accelerated atherosclerotic process seen in diabetics is associated with hypercholesterolemia (Boyle et al., supra.).

Dietary supplementation of chromium to normal individuals has been reported to lead to improvements in glucose tolerance, serum lipid concentrations, including high-density lipoprotein cholesterol, insulin and insulin binding (Anderson, *Clin. Psychol Biochem.* 4:31–41, 1986). Supplemental chromium in the trivalent form, e.g. chromic chloride, is associated with improvements of risk factors associated with adult-onset (type 2) diabetes and cardiovascular disease.

Chromium functions as a cofactor for insulin. It binds to the insulin receptor and potentiates many, and perhaps all, of its functions (Boyle et al., supra.). These functions include, but are not limited to, the regulation of carbohydrate and lipid metabolism. (*Present Knowledge in Nutrition*, supra, at p. 573–577). The introduction of inorganic chromium compounds per se into individuals is not particularly beneficial. Chromium must be converted endogenously into an organic complex or must be consumed as a biologically active molecule. Only about 0.5% of ingested inorganic chromium is assimilated into the body (*Recommended Daily Allowances*, Ninth Revised Edition, The National Academy of Sciences, page 160, 1980). Only 1–2% of most organic chromium compounds are assimilated into the body.

U.S. Pat. No. Re. 33,988 discloses that when selected essential metals, including chromium, are administered to mammals as exogenously synthesized coordination complexes of picolinic acid, they are directly available for absorption without competition from other metals. This patent describes a composition and method for selectively supplementing the essential metals in the human diet and for facilitating absorption of these metals by intestinal cells. These complexes are safe, inexpensive, biocompatible and easy to produce. These exogenously synthesized essential metal coordination complexes of picolinic acid (pyridine-2-carboxylic acid) have the following structural formula:

wherein M represents the metallic cation and n is equal to the cation's valence. For example, when M is Cr and n=3, then the compound is chromic tripicolinate. Other chromium picolinates disclosed include chromic monopicolinate and chromic dipicolinate.

The U.S. Recommended Daily Intake (RDI) of chromium is 120 µg. U.S. Pat. No. 5,087,623, the entire contents of which are hereby incorporated by reference, describes the administration of chromic tripicolinate for the treatment of adult-onset diabetes in doses ranging from 50 to 500 µg. International Patent Application No. WO96/35421 discloses the use of high doses of chromic tripicolinate (providing 1,000–10,000 µg chromium/day) for reducing hyperglycemia and stabilizing the level of serum glucose in humans with type 2 diabetes. U.S. Pat. No. 5,789,401 discloses a chromic tripicolinate-biotin composition and its use in lowering blood glucose levels in humans with type 2 diabetes.

U.S. Pat. Nos. 5,087,623; 5,087,624; and 5,175,156, the entire contents of which are hereby incorporated by reference, disclose the use of chromium tripicolinate for supplementing dietary chromium, reducing hyperglycemia and stabilizing serum glucose, increasing lean body mass and reducing body fat, and controlling blood serum lipid levels, including the lowering of undesirably high blood serum LDL-cholesterol levels and the raising of blood serum HDL-cholesterol levels. U.S. Pat. Nos. 4,954,492 and 5,194,615, the entire contents of which are hereby incorporated by reference, describe a related complex, chromic nicotinate, which is also used for supplementing dietary chromium and lowering serum lipid levels. Picolinic acid and nicotinic acid are position isomers having the following structures:

picolinic acid nicotinic acid

Nicotinic acid and picolinic acid form coordination complexes with monovalent, divalent and trivalent metal ions and facilitate the absorption of these metals by transporting them across intestinal cells and into the bloodstream. Chromium absorption in rats following oral administration of $CrCl_3$ was facilitated by the non-steroidal anti-inflammatory drugs (NSAIDs) aspirin and indomethacin (Davis et al., *J. Nutrition Res.* 15:202–210, 1995; Kamath et al., *J. Nutrition* 127:478–482, 1997). These drugs inhibit the enzyme cyclooxygenase which converts arachidonic acid to various prostaglandins, resulting in inhibition of intestinal mucus formation and lowering of intestinal pH which facilitates chromium absorption.

Additional pharmacological treatments for disorders caused by or exacerbated by improper glucose uptake are needed. Specifically, compositions for the treatment of diabetes and obesity would be a great boon to subjects suffering from these disease states. A new, more effective, less expensive treatment for diabetes and obesity with minimal side effects would be a great benefit to the treatment and prevention of obesity.

SUMMARY OF THE INVENTION

The disclosed invention is directed to compositions and methods for treating insulin-dependent diabetes, non-insulin dependent diabetes, reduction of body fat, improvement of insulin sensitivity, reduction of hyperglycemia, and reduction of hypercholesterolemia. One embodiment of the disclosed invention is a composition that includes at least one chromium complex and a conjugated fatty acid or conjugated fatty alcohol. Preferably, the chromium complex is chromium picolinate or chromium nicotinate. Advantageously, the conjugated fatty acid is conjugated linoleic acid.

In one aspect of the invention, the composition optionally includes a chelating agent. The chelating agent may be picolinic acid, nicotinic acid, or both.

The recited compositions are incorporated into a pharmaceutically effective carrier. The pharmaceutically effective carrier may be a tablet, capsule, microbead, emulsion, powder, granule, suspension, syrup or elixir. Preferably, when the carrier is a microbead, the microbead is a sugar beadlet or microcrystalline cellulose beadlet. Advantageously, the chromium complex and conjugated linoleic acid are coated on the beadlet. Optionally, the tablet, capsule, or microbead is coated with an enteric coating.

In another aspect of the invention, the chromium complex and conjugated fatty acid or conjugated fatty alcohol are in a ratio of between about 1:666 to about 1:200 (w/w).

Additional components may be included in the composition. For example, the composition may include at least one of a cyclooxygenase inhibitor, a mucolytic, or a salicin-containing herb. The cyclooxygenase inhibitor may be indomethacin, ibuprofen, acetaminophen, or naproxen. Advantageously, the salicin-containing herb may include *Boswellia serrata* (frankincense), *Betula lenta* (sweet birch), *Betula pubescens* (white birch), *Filipendula ulmaria* (meadowsweet), *Gautheria procumbens* (wintergreens), *Polulus balsamifera, Populusjackii* (balm of Gilead) and *Salix alba* (white willow). The mucolytic may be guaifenesin.

Embodiments of the invention provide a method of treating type 1 diabetes in a subject. The method of treatment includes administering to a subject a pharmaceutically effective dose of a conjugated fatty acid or conjugated fatty alcohol in conjunction with at least one chromium complex. The chromium complex may be chromium picolinate, chromium nicotinate, chromic tripicolinate, chromic polynicotinate, chromium chloride, chromium histidinate, or chromium yeasts. Optionally, the composition further includes at least one chelating agent. The chelating agent may be picolinic acid, nicotinic acid, or both.

A method of treating obesity in a subject is similarly contemplated. The method of treatment includes administering to a subject a pharmaceutically effective dose of conjugated fatty acid or conjugated fatty alcohol in conjunction with at least one chromium complex. The chromium complex may be chromium picolinate, chromium nicotinate, chromic tripicolinate, chromic polynicotinate, chromium chloride, chromium histidinate, or chromium yeasts. Optionally, the composition further includes at least one chelating agent. The chelating agent may be picolinic acid, nicotinic acid, or both.

DETAILED DESCRIPTION OF THE PREFERRED EMBODIMENT

The disclosed invention relates to compositions for the treatment of type 1 diabetes. In particular, these compositions can be administered to reduce or even eliminate the need for administration of insulin in certain patients with type 1 diabetes. Further, they are used in methods for facilitating glucose uptake and utilization by cells. Certain individuals with type 2 diabetes will require insulin. The invention also relates to the treatment of type 2 diabetics who require insulin. Additionally, methods for treating obesity and increasing lean body mass are likewise contemplated. A primary basis of the present invention is the novel and unexpected discovery that compositions comprising an effective dose of a chromium complex in combination with a conjugated fatty acid or conjugated fatty alcohol produce a synergistic effect on glucose uptake in a subject in need thereof. Additionally, the co-administration of a chromium complex with a conjugated fatty acid or conjugated fatty alcohol, or an isomer thereof, demonstrate a synergistic, weight loss effect.

The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the invention herein described.

The term "conjugated compound" refers to a compound having at least a portion that is a hydrocarbon, with at least three consecutive carbon—carbon bonds, such that single and double carbon—carbon bonds are found in an alternating manner. Thus, the compound will include the subunit C═C—C═C (hydrogens and other substituents not shown). Two preferred categories of conjugated compounds are fatty acids and fatty alcohols. It should be noted that these di- or poly-unsaturated compounds are referred to herein using the common names of the corresponding naturally-occurring compounds having the same number of carbons and unsaturations. Although such naturally-occurring compounds are not necessarily conjugated, due to the arrangement of their carbon—carbon double bonds, it will be understood in the context of the present invention that only conjugated versions of those compounds are contemplated; i.e., the arrangement of the double bounds will be such that they contain the substructure C═C—C═C. While compounds having as few as 4, 5, 6, or 7 carbon atoms are contemplated, the preferred conjugated compounds have 8, 9, 10, 12, 14, 16 or more carbon atoms, preferably not more than 32, 30, 28, or 26 carbon atoms. It should be noted that the phrase "conjugated fatty acid" or "conjugated fatty alcohol", as used herein, also includes isomers of fatty acids and fatty alcohols, as well as any other polyunsaturated compounds which act synergistically with chromium complexes to promote glucose uptake in a subject in need thereof. Suitable conjugated fatty acids include, without limitation, conjugated versions of linoleic acid, linolenic acid, gamma linolenic acid, arachidonic acid, mead acid, stearidonic acid, alpha-eleostearic acid, eleostearic acid, pinolenic acid, docosatetraenoic acid, 9,12-octadecadienoic acid, octadecatrienoic acid, eicosatetraenoic acid, eicosapentaenoic acid, docosahexaenoic acid, docosapentaenoic acid, and all other diunsaturated and polyunsaturated fatty acids. In a preferred embodiment, the conjugated fatty acid is conjugated linoleic acid (CLA). As used herein, the phrase "conjugated fatty alcohols" includes, without limitation, conjugated versions of linoleic alcohol, linolenic alcohol, gamma linolenic alcohol, arachidonic alcohol, mead alcohol, stearidonic alcohol alpha-eleostearic alcohol, eleostearic alcohol, pinolenic alcohol, docosadienic alcohol, docosatetraenoic alcohol, octadecadienoic alcohol, octadecatrienoic alcohol, eicosatetraenoic alcohol, eicosapentaenoic alcohol, docosahexaenoic alcohol, docosapentaenoic alcohol, and all other diunsaturated and polyunsaturated fatty alcohols. The present invention further includes the use of other conjugated compounds having at least 4, 5, 6, 7, or 8 carbon atoms, that functions synergistically with a chromium complex to facilitate glucose uptake and usage by cells. (Such function can be readily assayed, as further described below.) Note that the present invention includes alcohols and acids in which one or more of the double bonds result in a cis isomer, as well as those in which one or more of the double bonds result in a trans isomer. In some cases, all the double bonds are cis, while in others they are all trans, and in still other cases they are mixed cis and trans compounds.

In a preferred embodiment, the conjugated fatty acid of the composition is conjugated linoleic acid. Conjugated linoleic acid (CLA) has been reported in numerous publications to reduce fat gain in growing animals by 25%–70% (Park et al., 1997). Minimal studies have been performed on human subjects. In a preliminary study by Atkinson et al., there was no effect of CLA alone in obese subjects when added to standard diet and exercise. However, a subgroup of subjects who did not follow the diet and exercise program well, and who gained lean body mass, had a reduction in fat mass in the CLA subjects and an increase in fat mass in placebo subjects (Atkinson, communication, 2000). These data, along with the animal data, suggest that CLA is most effective in preventing fat accumulation rather than producing fat loss. Two hypotheses have been advanced to explain the role of CLA in weight loss: 1) CLA may act as a β-3 agonist; and 2) CLA alters nutrient partitioning within muscles to promote fat oxidation rather than carbohydrate (CHO) oxidation (Park et al., 1999).

Figure 1:
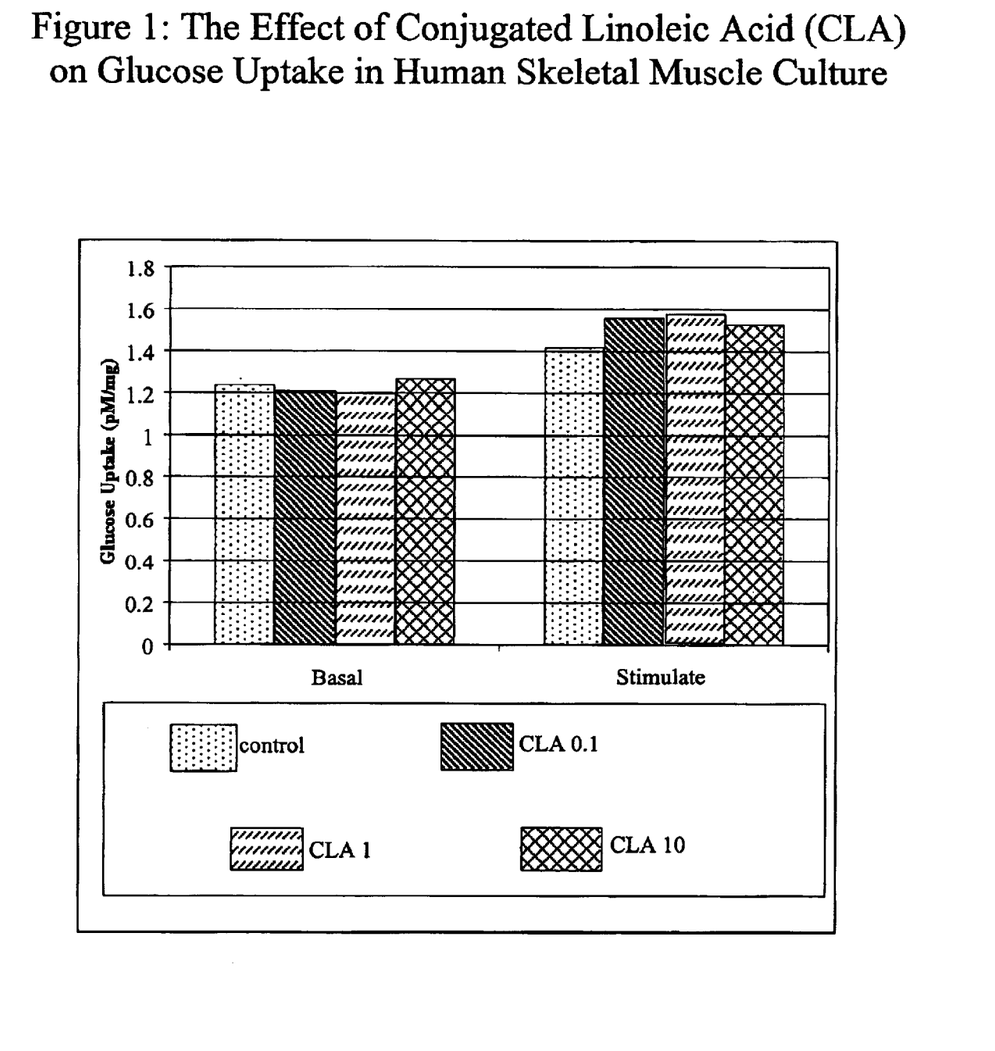
FIG. 1 shows the effect of conjugated linoleic acid (CLA) on glucose uptake in human skeletal muscle culture.
Figure 2:
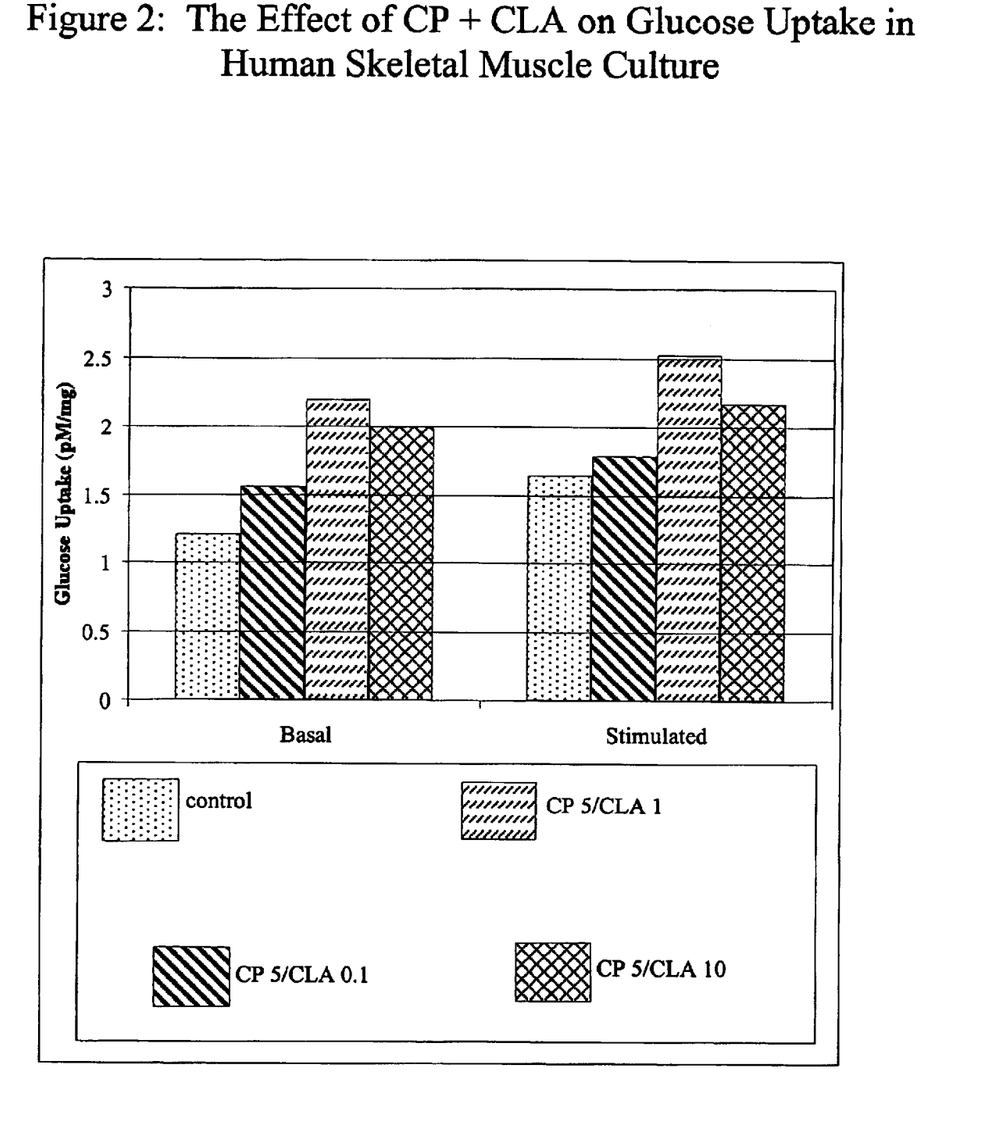
FIG. 2 graphs the effect of CP+CLA on glucose uptake in human skeletal muscle culture.
Figure 3:
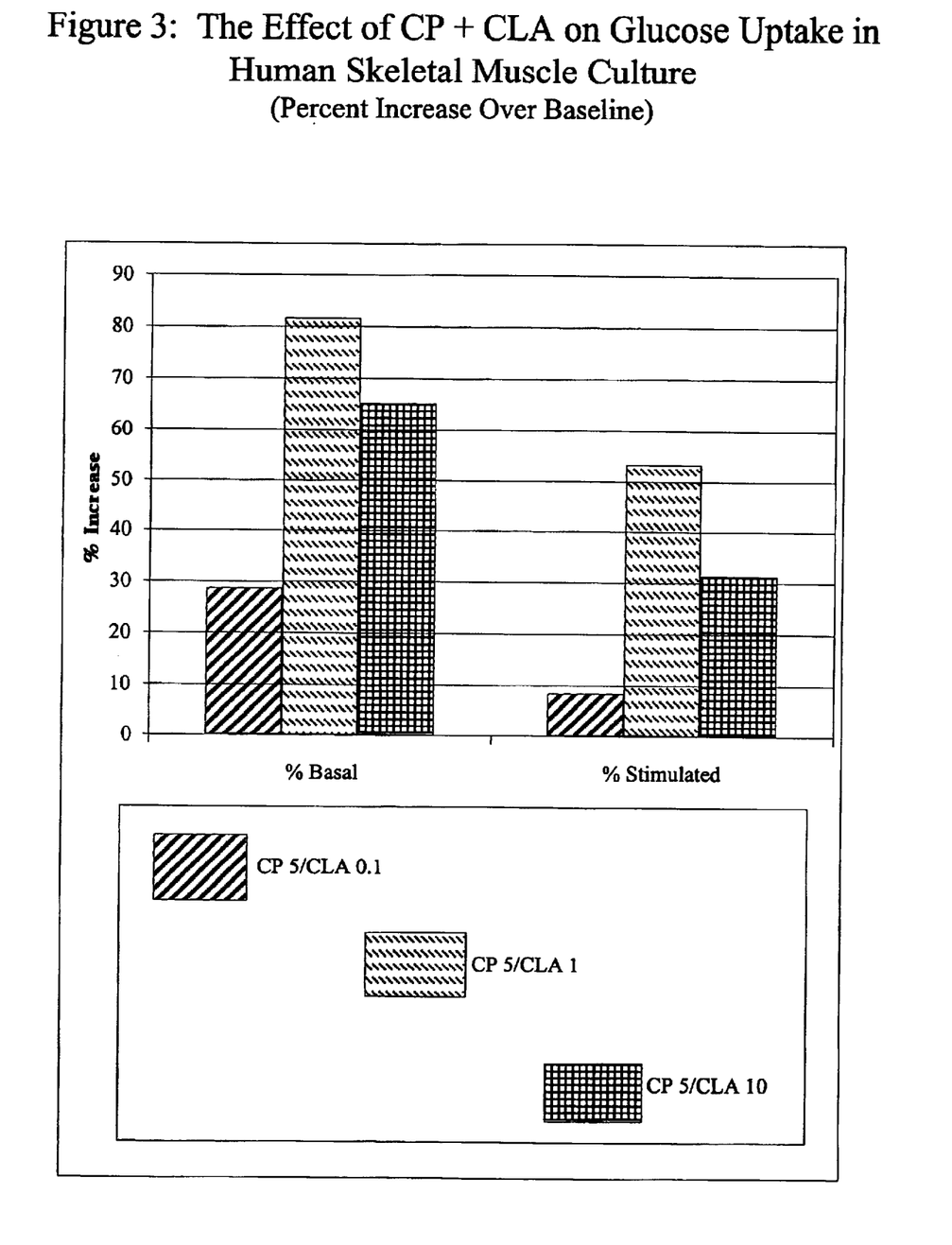
FIG. 3 illustrates the effect of CP+CLA on glucose uptake in human skeletal muscle culture.

Embodiments of the present invention include compositions which contain a conjugated fatty acid or conjugated fatty alcohol in combination with at least one chromium complex. Additionally, uses of the compositions disclosed herein to treat diabetes and/or obesity are provided. The co-administration of a conjugated fatty acid or conjugated fatty alcohol and at least one chromium complex provides a number of advantages over conventional pharmaceutical regimes for the treatment of diabetes and promotion of weight loss. One advantage of the compositions described herein over conventional treatment regimes for diabetes (such as injection of insulin) and weight loss is that compositions comprising a conjugated compound such as a conjugated fatty acid or conjugated fatty alcohol and at least one chromium complex have no known side effects while still providing efficacy in glucose uptake and weight loss. With reference to FIG. 1, one will observe that a conjugated fatty acid such as CLA alone had no effect on glucose uptake in human skeletal muscle culture under both basal (without insulin) and stimulated (with insulin) conditions. The units referred to on the vertical axis of FIGS. 1 and 2 are pico Moles per milligram of glucose uptake. The unit referred to on the vertical axis of FIG. 3 is the percentage increase in the uptake of glucose in human skeletal muscle culture. The term Basal as used in FIGS. 1 and 2 refers to human skeletal muscle culture without insulin. Whereas the term Stimulated indicates human skeletal muscle culture with insulin. Those bars on FIGS. 1, 2, and 3 representing Chromium Picolinate (CP) and Conjugated Linoleic Acid (CLA) are measured in nanograms per milliliter.

However, the administration of CLA in combination with a chromium complex such as chromium picolinate (CP) (as depicted in FIG. 2) significantly increases glucose uptake in human skeletal muscle culture under both basal (without insulin) and stimulated (with insulin) conditions. CP and CLA under basal conditions was shown to have a greater effect than insulin alone.

Finally, turning to FIG. 3, it will be appreciated that CLA plus a chromium complex synergistically aid in the percent increase in the uptake of glucose in human skeletal muscle culture.

In some embodiments, compositions comprising an effective dose of a chromium complex are provided. As used herein, the terms "chromium complexes" or "chromium complex" include, without limitation, chromium picolinate, chromic tripicolinate, chromium nicotinate, chromic polynicotinate, chromium chloride, chromium histidinate, and chromium yeasts. Chromium picolinate, for example, has been shown to produce modest weight loss and changes in body composition.

The compositions of the disclosed invention additionally include an effective dose of conjugated compound such as a conjugated fatty acid or conjugated fatty alcohol, of the type previously described. In preferred embodiments, the conjugated fatty acid component of the composition is linoleic acid (CLA). Suitable forms of CLA include isomers with double bonds at carbons 9, 11; carbons 10, 12; or a mixture thereof Preferably, the compositions include the 10, 12 form of CLA to reduce body fat and increase lean body mass. Advantageously, the composition will include the conjugated compound at a dose of at least 50% by weight of formulation. More preferably, the effective dose of the conjugated compound for a 70 kg human is between about 100 mg to about 10 grams. In a most preferred embodiment, the effective dose of the conjugated compound is 75 mg, 100 mg, 250 mg, 500 mg, 750 mg, 1000 mg, 2 g, 5 g, 7 g, or 10 g.

While the chromium complexes aid in the absorption of chromium by intestinal cells, in some embodiments, chelating agents are advantageously included in the compositions to facilitate absorption of other ingested chromium as well as other metals including, but not limited to, copper, iron, magnesium, manganese and zinc. Suitable chelating agents include picolinic acid, nicotinic acid, or both picolinic acid and nicotinic acid. Thus, the compositions of the disclosed invention are readily absorbable forms of chromium which also facilitate absorption of other essential metals in the human diet.

The chromium complexes of the disclosed invention have the same uses as described for chromic tripicolinate in U.S. Pat. Nos. 5,087,623, 5,087,624 and 5,174,156, namely supplementing dietary chromium, lowering blood glucose levels in diabetics, lowering serum lipid levels and increasing lean body mass. Additionally, the chromium complexes of the present invention act to treat symptoms associated with overweight and obesity.

Advantageously, the chromium complexes are synthetic. The synthesis and use of chromium picolinates is described in U.S. Pat. Nos. Re. 33,988 and 5,087,623. Chromic tripicolinate is available from health food stores, drug stores and other commercial sources. The synthesis and use of chromic polynicotinate is described in U.S. Pat. No. 5,194,615.

The chelating agents such as picolinic acid and nicotinic acid are available from many commercial sources, including Sigma-Aldrich (St. Louis, Mo.) (picolinic acid; catalog No. P5503; nicotinic acid; catalog No. PN4126). Preferably, the ratio of the chromium complex to the chelating agent from about 10:1 to about 1:10 (w/w), more preferably from about 5:1 to about 1:5 (w/w).

A variety of delivery systems are available to deliver the compositions to a subject in need thereof. Preferably, the compositions of the disclosed invention are prepared by incorporating the components into a pharmaceutically acceptable carrier, including but not limited to tablets, capsules and microbeads, preferably sugar beadlets or microcrystalline cellulose.

For oral administration, the chromium complex may be incorporated into a tablet, aqueous or oil suspension, dispersible powder or granule, microbead, emulsion, hard or soft capsule, syrup or elixir. The components of the composition may also be administered separately. Compositions may be prepared according to any method known in the art for the manufacture of pharmaceutically acceptable compositions and such compositions may contain one or more of the following agents: sweeteners, flavoring agents, coloring agent and preservatives. Tablets containing the active ingredients in admixture with non-toxic pharmaceutically acceptable excipients suitable for tablet manufacture are acceptable. "Pharmaceutically acceptable" means that the agent should be acceptable in the sense of being compatible with the other ingredients of the formulation (as well as non-injurious to the individual). Such excipients include inert diluents such as calcium carbonate, sodium carbonate, lactose, calcium phosphate or sodium phosphate; granulating and disintegrating agents, such as corn starch and alginic acid; binding agents such as starch, gelatin or acacia; and lubricating agents such as magnesium stearate, stearic acid or talc. Tablets may be uncoated or may be coated with known techniques to delay disintegration and absorption in the gastrointestinal tract and thereby provide a sustained action over a longer period of time. For example, a time delay material such as glyceryl monostearate or glyceryl stearate alone or with a wax may be employed.

In another preferred embodiment, tablets, capsules or microbeads are coated with an enteric coating which prevents dissolution in the acidic environment of the stomach. Instead, this coating dissolves in the small intestine at a more neutral pH. Because certain chromium complexes may be more stable at this neutral pH than at the acidic pH of the stomach, enhanced absorption occurs because the chromium complexes remain substantially intact until they reach the small intestine. Such enteric coated compositions are described by Bauer et al., *Coated Pharmaceutical Dosage Forms: Fundamentals, Manufacturing Techniques, Biopharmaceutical Aspects, Test Methods and Raw Materials*, CRC Press, Washington, D.C., 1998, the entire contents of which are hereby incorporated by reference.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the chromium complexes of the invention in admixture with excipients for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agent, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, may also be present.

Syrups and elixirs may be formulated with sweetening agents, such as glycerol, sorbitol or sucrose. Such formulations may also contain a demulcent, a preservative, a flavoring or a coloring agent.

The oral formulations described above may also include aspirin (acetylsalicylic acid), other salicylates, or another NSAID such as indomethacin, ibuprofen, acetaminophen, naproxen or any drug capable of inhibiting the cyclooxygenase pathway leading to prostaglandin synthesis. This results in a decrease in intestinal mucus production and lower intestinal pH which facilitates absorption of the chromium compositions of the present invention. The oral compositions may further include mucolytics such as guaifenesin and the like, to inhibit intestinal mucus production, and/or acids such as ascorbic acid, citric acid and the like to lower intestinal pH. Inclusion of one or both of these compounds further enhances chromium absorption. There are two forms of cyclooxygenase (cox), cox1 and cox2, which differ in their sensitivity to inhibition by NSAIDs. The cox2 isozyme promotes prostaglandin formation at sites of inflammation, but not at other sites such as the gastrointestinal tract. In contrast, relatively selective inhibition of cox1 facilitates chromic tripicolinate and chromic polynicotinate absorption. Although the selective inhibition of cox1 is desirable, any inhibitor or cox1 or cox2 can be formulated with the chromic tripicolinate and chromic polynicotinate compositions of the invention. Cox inhibitors, acids and mucolytics may also be coadministered with the chromic tripicolinate and chromic polynicotinate compositions of the invention. The amount of these drugs formulated with or coadministered with the chromic tripicolinate compositions of the invention are as follows: cox inhibitions, between about 50 mg and 500 mg; mucolytics, between about 10 mg and 250 mg; and acids, between about 50 mg and about 1,000 mg.

The coadministration or formulation of salicylate-containing herbs with the compositions of the invention is also contemplated. Class I herbs, as documented in the American Herbal Products Association's *Botanical Safety Handbook* (herbs that can be safely consumed when used appropriately), such as Boswelia serrata (frankincense), *Betula lenta* (sweet birch), *Betula pubescens* (white birch), *Filipendula ulmaria* (meadowsweet), *Gaultheria procumbens* (wintergreens), *Populus balsamifera* and *Populus jackii* (balm of Gilead), and *Salix alba* (white willow) are all salicin-containing plants with salicylate-like properties. These herbs suppress prostaglandin synthesis by cox inhibition, thereby improving absorption of the chromium complexes of the invention. These herbs are relatively free from gastric ulcerogenic effects (Singh et al., *Agents and Actions* 18:407–412, 1986). In addition, pre-clinical acute toxicity studies have shown that salicin-containing plants do not cause hematological disturbances (American Herbal Products Association, *Botanical Safety Handbook*, 1997).

The compounds and herbs described above all effect gut physiology by inhibiting prostaglandin synthesis, decreasing mucus production, and lowering gastrointestinal pH. The inclusion of these compounds, as well as an enteric coating, into the oral chromium picolinate or chromium nicotinate compositions of the invention results in a multicomponent delivery system which allows delivery of these agents to the gastrointestinal tract where they work in concert to facilitate chromium absorption.

In a preferred embodiment, the chromium complex is coated onto microbeads. In a particularly preferred embodiment, these microbeads are sugar beadlets of various sizes, also known as nonpareils, and are commercially available from, for example, SmithKline Beecham. If the microbeads are to be used to administer the compositions of the invention to diabetic patients, the administration of other types of microbeads, such as microcrystalline cellulose, is preferred. Microcrystalline cellulose is commercially available and can be processed into beadlets of various sizes by micronization, a technique well known in the art. The microbeads are essentially a carrier for the compositions of the invention. For a description of coated beadlets, see, for example, Carstensen, J. T., *Pharmaceutical Principles of Solid Dosage Forms*, Technonic Publishing Co., Inc., Lancaster, Pa., pp. 228–230, 1993, hereby incorporated by reference. Aqueous solutions containing the chromium complexes with or without the chelating agent components such as nicotinic acid and picolinic acid are sprayed onto the microbeads by well known methods by suspending the microbeads in an up current of air and introducing a fine spray of the active ingredients which form a coating on the outside of the microbeads which is then allowed to dry. The desired chromium complex components with or without a chelating agent may be combined into one same solution or applied using separate solutions. Optionally, the coated microbeads can be further coated with a substance to protect the active ingredients coated onto the beads, such as latex. The microbeads may be placed in a capsule prior to administration. In another preferred embodiment, the capsule or the microbeads are coated with an enteric coating to delay dissolution until reaching the small intestine.

Typically, the dosage range of chromium administered to an individual in the form of chromium picolinate, chromium nicotinate, or other chromium complex provides between about 50 and 10,000 micrograms per day of chromium; preferably between about 100 and 1,000 micrograms per day; more preferably, between about 200 and 500 micrograms per day.

In some embodiments, methods of increasing glucose uptake by cells or by organisms, such as mammals and humans, treating insulin-dependent diabetes, reducing body fat, improving insulin sensitivity, reducing hyperglycemia, and reducing hypercholesterolemia with chromium complexes and conjugated compounds such as conjugated fatty acids or conjugated fatty alcohols are contemplated and isomers of fatty acids, as well as isomers of fatty alcohols. Advantageously, a subject is administered a pharmaceutically effective dose of a chromium complex. In one embodiment, the conjugated compound is administered substantially simultaneously with the chromium complex. In an alternative embodiment, the chromium complex is administered first and then the conjugated compound is added second. In yet another embodiment, the conjugated compound is administered first. Preferably, the chromium complex and conjugated compound are administered to a subject within twenty-four hours of each other. In a particularly preferred embodiment, the chromium complex and conjugated compound are administered within an hour of each other.

The following examples teach certain methods and compositions for treating diabetes and obesity through the administration of at least one chromium complex in concert with a conjugated compound. The subject can advantageously be a vertebrate, a mammal, a bird, and is preferably a human, a cat, or a dog. It will be appreciated, however, that the at least one chromium complex may be administered first, then the conjugated compound. Alternatively, the conjugated compound can be administered first, then the chromium complex. As illustrated in the following examples, the composition may optionally include picolinic acid, nicotinic acid, or both picolinic acid and nicotinic acid in combination with a chromium complex and conjugated compound. These examples are illustrative only and are not intended to limit the scope of the invention disclosed herein. The treatment methods described below can be optimized using empirical techniques well known to those of ordinary skill in the art. Moreover, artisans of skill would be able to use the teachings described in the following examples to practice the full scope of the invention disclosed herein.

EXAMPLE 1

An obese adult human subject is identified. The subject is orally administered a tablet containing about 300 μg chromium as chromium picolinate and 1 gram conjugated linoleic acid twice a day. The tablet additionally comprises ibuprofen in a pharmaceutically effective dose of 200 mg. Over the course of several weeks, a decrease in body mass is observed. The chromium picolinate in combination with conjugated linoleic acid synergistically reduce the subject's body mass.

It will be appreciated that although specific embodiments of the invention have been described herein for the purposes of illustration, various modifications may be made without deviating from the spirit and scope of the invention. Accordingly, the invention is not limited except as by the appended claims.

EXAMPLE 2

A subject suffering from insulin-dependent diabetes is identified. The subject is orally administered a daily dose of one tablet containing about 500 μg chromium as chromium nicotinate and 500 mg conjugated linoleic acid. Over the course of several days, an improvement in glucose uptake in the subject is observed and insulin dependence is reduced. The chromium nicotinate in combination with linoleic acid act synergistically to improve the subject's glucose tolerance and to treat the subject's diabetes.

What is claimed is:

1. A composition for reducing body fat, improving insulin sensitivity, reducing hyperglycemia, promoting weight loss, and reducing hypercholesterolemia, said composition consisting essentially of at least one chromium complex and a conjugated linoleic acid or conjugated linoleic alcohol.

2. The composition of claim 1, wherein said chromium complex is chromium picolinate or chromium nicotinate.

3. The composition of claim 1, wherein said chromium complex and said conjugated linoleic acid or conjugated linoleic alcohol are in a ratio of between about 1:3000 to 1:50 (w/w).

4. The composition of claim 1, wherein said composition is incorporated into a pharmaceutically effective carrier.

5. The composition of claim 4, wherein said pharmaceutically effective carrier is selected from the group consisting of a tablet, capsule, microbead, emulsion, powder, granule, suspension, syrup and elixir.

6. The composition of claim 5, wherein said microbead is a sugar beadlet or microcrystalline cellulose beadlet and said at least one chromium complex and said conjugated linoleic acid are coated on said beadlet.

7. The composition of claim 5, wherein said tablet, capsule, or microbead is coated with an enteric coating.

8. A composition for reducing body fat, improving insulin sensitivity, reducing hyperglycemia, promoting weight loss, and reducing hypercholesterolemia, said composition consisting essentially of at least one chromium complex, a conjugated linoleic acid or conjugated linoleic alcohol, and a chelating agent.

9. The composition of claim 8, wherein said chelating agent is picolinic acid, nicotinic acid, or both.

10. A composition for reducing body fat, improving insulin sensitivity, reducing hyperglycemia, promoting weight loss, and reducing hypercholesterolemia, said composition consisting essentially of at least one chromium complex, a conjugated linoleic acid or conjugated linoleic alcohol, and at least one of a cyclooxygenase inhibitor a mucolytic, and a salicin-containing herb.

11. The composition of claim 10, wherein said cyclooxygenase inhibitor is selected from the group consisting of indomethacin, ibuprofen, acetaminophen, and naproxen.

12. The composition of claim 10, wherein said salicin-containing herb is selected from the group consisting of *Boswellia serrata* (frankincense), *Betula lenta* (sweet birch), *Betula pubescens* (white birch), *Filipendula ulmaria* (meadowsweet), *Gautheria procumbens* (wintergreens), *Polulus balsamifera*, *Populus jackii* (balm of Gilead) and *Salix alba* (white willow).

13. The composition of claim 10, wherein said mucolytic is guaifenesin.

* * * * *